US008124075B2

(12) United States Patent
Burkinshaw et al.

(10) Patent No.: US 8,124,075 B2
(45) Date of Patent: Feb. 28, 2012

(54) ENHANCED BIOLOGICAL AUTOLOGOUS TISSUE ADHESIVE COMPOSITION AND METHODS OF PREPARATION AND USE

(75) Inventors: Brian D. Burkinshaw, Pflugerville, TX (US); Steven I. Whitlock, Austin, TX (US); James B. Rogan, Austin, TX (US); Gerald L. Devries, Austin, TX (US)

(73) Assignee: Spinal Restoration, Inc., Austin, TX (US)

( * ) Notice: Subject to any disclaimer, the term of this patent is extended or adjusted under 35 U.S.C. 154(b) by 967 days.

(21) Appl. No.: 11/181,677

(22) Filed: Jul. 14, 2005

(65) Prior Publication Data
US 2008/0206298 A1   Aug. 28, 2008

Related U.S. Application Data

(60) Provisional application No. 60/588,550, filed on Jul. 16, 2004.

(51) Int. Cl.
| | | |
|---|---|---|
| A61K 38/36 | (2006.01) | |
| A61M 5/00 | (2006.01) | |
| A61M 31/00 | (2006.01) | |
| A61M 37/00 | (2006.01) | |

(52) U.S. Cl. .................. 424/94.64; 604/191; 604/502; 604/506

(58) Field of Classification Search .................. None
See application file for complete search history.

(56) References Cited

U.S. PATENT DOCUMENTS

| | | | | |
|---|---|---|---|---|
| 2,533,004 A | 12/1950 | Ferry et al. | .................. | 260/112 |
| 3,089,815 A | 5/1963 | Lieb et al. | .................. | 167/58 |
| 4,359,049 A * | 11/1982 | Redl et al. | .................. | 604/82 |
| 4,393,041 A | 7/1983 | Brown et al. | .................. | 424/19 |
| 4,427,650 A | 1/1984 | Stroetmann | .................. | 424/46 |
| 4,442,655 A | 4/1984 | Stroetmann | .................. | 53/428 |
| 4,619,913 A | 10/1986 | Luck et al. | .................. | 514/131 |
| 4,874,368 A * | 10/1989 | Miller et al. | .................. | 604/82 |
| RE33,375 E | 10/1990 | Luck et al. | .................. | 514/2 |
| 5,116,315 A * | 5/1992 | Capozzi et al. | .................. | 604/82 |
| 5,124,155 A | 6/1992 | Reich | .................. | 424/428 |
| 5,264,446 A | 11/1993 | Hegasy et al. | .................. | 514/356 |
| 5,290,552 A | 3/1994 | Sierra et al. | .................. | 424/94.64 |
| 5,585,007 A * | 12/1996 | Antanavich et al. | .................. | 210/782 |
| 5,643,192 A | 7/1997 | Hirsh et al. | .................. | 604/4 |
| 5,651,982 A | 7/1997 | Marx | .................. | 424/450 |
| 5,702,715 A | 12/1997 | Nikolaychik et al. | .................. | 424/402 |
| 5,795,571 A * | 8/1998 | Cederholm-Williams et al. | .................. | 424/94.64 |
| 5,925,738 A | 7/1999 | Miekka et al. | .................. | 530/380 |
| 5,962,420 A | 10/1999 | Edwardson et al. | .................. | 514/21 |
| 5,980,504 A | 11/1999 | Sharkey et al. | .................. | 604/510 |
| 5,980,866 A | 11/1999 | Uchida et al. | .................. | 424/45 |
| 6,007,570 A | 12/1999 | Sharkey et al. | .................. | 607/96 |
| 6,007,811 A | 12/1999 | Sawyer et al. | .................. | 424/94.64 |
| 6,054,122 A | 4/2000 | MacPhee et al. | .................. | 424/94.4 |
| 6,073,051 A | 6/2000 | Sharkey et al. | .................. | 607/99 |
| 6,117,425 A | 9/2000 | MacPhee et al. | .................. | 424/94.64 |
| 6,122,549 A | 9/2000 | Sharkey et al. | .................. | 607/99 |
| 6,124,273 A | 9/2000 | Drohan et al. | .................. | 514/55 |
| 6,126,682 A | 10/2000 | Sharkey et al. | .................. | 607/96 |
| 6,183,518 B1 | 2/2001 | Ross et al. | .................. | 623/17.16 |
| 6,197,325 B1 | 3/2001 | MacPhee et al. | .................. | 424/426 |
| 6,258,086 B1 | 7/2001 | Ashley et al. | .................. | 606/41 |
| 6,261,311 B1 | 7/2001 | Sharkey et al. | .................. | 607/96 |
| 6,280,727 B1 * | 8/2001 | Prior et al. | .................. | 424/94.63 |
| 6,320,029 B1 | 11/2001 | Miekka et al. | .................. | 530/380 |
| 6,428,576 B1 | 8/2002 | Haldimann | .................. | 623/17.16 |
| 6,517,568 B1 | 2/2003 | Sharkey et al. | .................. | 607/96 |
| 6,547,810 B1 | 4/2003 | Sharkey et al. | .................. | 607/96 |
| 6,559,119 B1 | 5/2003 | Burgess et al. | .................. | 514/2 |
| 6,638,276 B2 | 10/2003 | Sharkey et al. | .................. | 606/41 |
| RE38,431 E | 2/2004 | Miekka et al. | .................. | 530/380 |
| 6,726,685 B2 | 4/2004 | To et al. | .................. | 606/50 |
| 6,733,496 B2 | 5/2004 | Sharkey et al. | .................. | 606/41 |
| 6,749,605 B2 | 6/2004 | Ashley et al. | .................. | 606/41 |
| 6,749,617 B1 * | 6/2004 | Palasis et al. | .................. | 606/181 |
| 6,762,336 B1 | 7/2004 | MacPhee et al. | .................. | 602/48 |
| 6,767,347 B2 | 7/2004 | Sharkey et al. | .................. | 606/41 |
| 6,921,532 B1 | 7/2005 | Austin et al. | .................. | 424/94.64 |
| 2003/0181964 A1 | 9/2003 | Sharkey et al. | .................. | 607/96 |
| 2004/0111136 A1 | 6/2004 | Sharkey et al. | .................. | 607/99 |
| 2004/0193151 A1 | 9/2004 | To et al. | .................. | 606/41 |

FOREIGN PATENT DOCUMENTS

| | | |
|---|---|---|
| DE | 3037270 | 5/1981 |
| EP | 0 068 149 | 5/1982 |
| WO | WO81/00516 | 3/1981 |
| WO | WO92/22312 | 12/1992 |
| WO | WO94/20133 | 9/1994 |
| WO | WO96/17633 | 6/1996 |
| WO | WO97/42986 | 11/1997 |

OTHER PUBLICATIONS

US 6,645,204, 11/2003, Sharkey et al. (withdrawn).
Abstract: T. Yagita, "Agent for Controlling Formation of Cheloid at Excision Site for Inflammation Bowel Disease" Feb. 10, 1997; Database WPI, Section Ch, Week 199716, Derwent Publications Ltd., London, GB XP002182938.
Abstract: Sumitomo Cement Co., "Sustained Release Agent for Treatment of Osteomyelitis" Jan. 8, 1993; Database WPI, Section Ch, Week 199306, Derwent Publications Ltd., London, GB XP002 I 82939.
G. Y. Bong et al., "Development of Local Antibiotic Delivery System Using Fibrin Glue" Mar. 1, 1996; Journal of Controlled Release, Elsevier Science Publishers, vol. 29, No. 1, pp. 65-70.
J. Rousou et al., "Randomized Clinical Trial of Fibrin Sealant in Cardiac Surgery Patients Undergoing Resternotomy" Feb. 1989; Journal of Thoracic and Cardiovascular Surgery; vol. 97, No. 2, pp. 194-203.

(Continued)

*Primary Examiner* — Laura J Schuberg
(74) *Attorney, Agent, or Firm* — O'Keefe, Egan, Peterman & Enders, LLP

(57) ABSTRACT

The invention includes a composition useful for preparing a tissue sealant for use on a patient, comprising: autologous fibrinogen, an activating agent and at least one supplement. The invention includes a method of treating a disc having at least one defect, comprising: introducing a composition into the disc, wherein the composition comprises autologous fibrinogen and an activating agent, and wherein the composition forms fibrin.

5 Claims, No Drawings

OTHER PUBLICATIONS

P. Knoringer, "Fibrin Sealing in Spinal Neurosurgery" 1986.
P.M. McCarthy et al., "Fibrin Sealant: The Cleveland Clinic Experience" 1991.
M. Dahan et al., "The Importance of Biological Glue for the Prevention of Air Leakage in Pulmonary Surgery" 1991; Materials and Methods, pp. 113-116.
H. W. Waclawiczek, "Fibrin Sealing in Liver and Spleen Surgery" 1994.
C. Shaffey et al., "Neurosurgical Applications of Fibrin Glue: Augmentation of Dural Closure in 134 Patients" 1990; Neurosurgery, vol. 26, No. 2, pp. 207-210.
M. Acqui et al., "Our Experience With Human Fibrin Glue in Neurological Procedures" Date unknown.
A. Hjortrup, M.D. et al., "Fibrin Adhesive in Perineal Fistulas" Sep. 1991; from the Dept. of Surgical Gastroenterology F, Bispebjerg Hospital and Dept. of Surgical Gastroenterology C, Rigsbospitalet, University of Copenhagen, Copenhagen, Denmark, vol. 34, No. 9.
T. M. Kieser et al., "Reduced Postoperative Bleeding Following Use of Tisscel Fibrin Sealant in 300 Patients undergoing Open-Heart Surgery" date unknown.
W. D. Sponitz, M.D. et al., "Clinical Uses of Fibrin Sealant" 1999; Transfusion Therapy: Clinical Principles and Practice, Bethesda, MD: AABB Press.
N. Tajima et al., "Bone Grafts Using Fibrin Glue for Posterolateral Spinal Fusion and Total Hip Replacement with Central Migration" date unknown.
G. E. Lutz et al., "Flouroscopic Transforaminal Lumbar Epidural Steroids: An Outcome Study" Nov. 1998; Arch Phys Med Rehabil, vol. 79, pp. 18-21.
P. Goupille et al., "The Role of Inflammation in Disk Herniation-Associated Radiculopathy" Aug. 28, 1998; Semin Arthritis Rheum, (1):60-71.
J. D. Kang et al., "Herniated Lumbar Intervertebral Discs Spontaneously Produce Matrix Metalloproteinases, Nitric Oxide, Interleukin-6, and Prostaglandin E2" Feb. 1, 1996; Spine, 21(3): 271-7.
J. S. Seal et al., "High Levels of Inflammatory Phospholipase A2 Activity in Lumbar Disc Herniations" Jul. 1990; Spine, 15(7): 674-8.
O. P. Nygaard et al., "The Inflammatory Properties of Contained and Noncontained Lumbar Disc Herniation" Nov. 1, 1997; Spine, 22(21): 2484-8.
H. Takahashi et al., "Inflammatory Cytokines in the Herniated Disc of the Lumbar Spine" Jan. 15, 1996; Spine, 21(2):218-24.
Product Information, "Celestone Soluspan", brand of betamethasone sodium phosphate and betamethasone acetate Injectable Suspension, USP 6 mg. per mL, Schering Corporation, Kenilworth, N.J. 07033 USA, Rev. Mar. 1996.
Product Information, "Fibrin Sealant Hemaseel APR Kit, Two Component Fibrin Sealant, Vapor Heated, Kit" Manufactured for and Distributed by Haemacure Corp., 2 N. Tamiami Trail, Suite 802, Sarasota, FL 34236, Issued May 1998.

* cited by examiner

ENHANCED BIOLOGICAL AUTOLOGOUS TISSUE ADHESIVE COMPOSITION AND METHODS OF PREPARATION AND USE

This application claims priority to U.S. provisional application Ser. No. 60/588,550, filed Jul. 16, 2004, incorporated herein by reference.

FIELD OF THE INVENTION

The disclosure herein generally relates to an invention and method for the preparation and use of novel enhanced autologous biological tissue adhesives which are in one embodiment prepared in the absence of externally supplied thrombin.

BACKGROUND OF THE INVENTION

Fibrin sealants are well known and extensively used in clinical settings to promote hemostasis, i.e., the prevention of blood loss through coagulation, the formation of a blood clot. Fibrin sealants are commonly used as adjuncts to conventional surgical techniques such as suturing and cautery to control bleeding when the aforementioned techniques are found to be ineffective or impractical. Fibrinogen and fibrin have been known to play a major role in wound healing and in blood coagulation for many years. Bergel, in 1909, used fibrin powder to seal the wall of a blood vessel (Schwartz S I, Shires G T, Spencer F C, et al. Principles of surgery $7^{th}$ ed. McGraw Hill Co 1999; PP: 77-100). In cerebral surgery, fibrin was used for hemostasis as early as 1915 (Grey EG: Fibrin as a hemostatic in cerebral surgery. *Surg Gynecol Obstet* 1915; 21:452-4.). Young et al., have used fibrinogen to unite peripheral nerves (Young J Z, Medawar P B: Fibrin suture of peripheral nerves. *Lancet* 1940; 2:126). Tarlov and Bernard have also reported on the use of plasma clot to do the same (Tarlov IM, Bernard B: Plasma clot and silk suture of the nerves. *Surg Gynecol Obstet* 1943; 76:366.). However, in 1944 Cronkite et al. (CRONKITE LEP., LOZNER LEL., DEAVER CJM. Use of thrombin and fibrinogen in skin grafting. *J. Amer. Med. Assoc.*, 1944, 124, 976-8.) were unsuccessful in the use of fibrinogen and thrombin in skin grafts in humans. According to Lerner and Binur (LERNER R., BINUR NS. Current status of surgical adhesives. *J. Surg. Res.*, 1990, 48, 165-81), these and other studies were not successful, probably due to the use of low concentrations of fibrinogen. As a result, the use of this biological adhesive did not become popular until the 1970s.

Matras et al. in 1972, revived the interest in the use of fibrin for anastomosis of the nerves by increasing fibrinogen concentration (Matras H, Chiari F: Zur klebung von mikrogefassanastomosen, Proceedings, $13^{th}$ Annual meeting, Dtsch Ges. F. Plast und wiederherstellungschirurgie. *Thieme* 1977; PP: 357). Kunderna in 1975, used autogenous cryoprecipitate to reconnect human digital nerves (Kunderna H, Matras H: Die Klinische anwendung der klebung von Nervananastomosen bei der Rekonstruktion verletzter peripherer Nervan. *Wien Klin Wochenschr* 1975, 87:495). Eventually, fibrin glue was found to be effective in sealing dural defects, splenic rupture and visceral organ tears. In 1976, Spangler and co-workers did the same in cardiac surgery (Spangler H P, Braun F: Die lokale anwendung von fibrinogen und kollagen zur blustillung der herzchirurgie. *Wien Med Wochenschr* 1976; 126:86). Fibrin glue was also found to be useful in enhancing bone repair, healing skin incisions, nerve grafting and for sealing mastoid and frontal cavities (Lerner R, Binur N S: Current research review-Current status of surgical adhesives. *J Surg Res* 1990; 48:165-81). Subsequently, fibrin glue has been widely used in nearly all surgical fields for hemostasis or tissue union (Blair S D, Backhouse C M, Harper R, et al: Comparison of absorbable materials for surgical haemostasis. *Br J Surg* 1988; 75: 969-71).

Early use of fibrin sealants had limited successes and sometimes frequent failures, primarily due to the methods of production from autologous human fibrinogen which produced inconsistent quality and quantity of fibrin sealant in the clinical setting. These early approaches relied solely on in-vivo concentrations of fibrinogen and thrombin, which produced varying levels of quality and quantity from each patient, resulting in a fibrin clot that was unpredictable. This improved slightly in 1944 when researchers mixed fibrinogen with bovine thrombin in an attempt to accelerate the formation of the fibrin clot. This was an improvement, but without the benefit of fractionation technology to purify and improve the concentration of the fibrinogen and fibrinogenic components, results were still not consistent.

The method of adding bovine thrombin however had its own drawbacks; that is, the chance of blood-borne transmission of transmissible diseases. During the early 1980s, wide acceptance of plasma products in the United States was significantly reduced due to the risk of contamination by the AIDS virus. The development of a commercial fibrin sealant product for the U.S. market became prohibitive, pending advances in pooled-plasma purification and viral-detection methodologies. Although several fibrin tissue sealants utilizing bovine thrombin were approved and clinically used in Europe for many years, the US Food and Drug Administration (FDA) only approved the first such product for use in the US in May, 1998 (FDA Product Approval Letter, Reference Numbers: 87-0508 and 87-0509).

During this period of advanced fibrin sealant development, various improvements were considered for the preparation and clinical applications of fibrin sealants. Hirsh et al., U.S. Pat. No. 5,643,192 describes autologous fibrin glue including a fibrinogen component and a thrombin component, both prepared from a single donor plasma source. Hirsh, however, does not envision utilizing anything other than the donor's own thrombin as the clotting agent. MacPhee et al. U.S. Pat. No. 6,117,425 describes the supplementation of fibrin sealant with one or more compositions whereby the fibrinogen forms a fibrin matrix when in the presence of thrombin, $Ca^{++}$ and water and allows the added composition to be released from the fibrin matrix over a sustained period that is greater than the period obtained according to simple diffusion kinetics. Similarly, Marx U.S. Pat. No. 5,651,982 describes supplemented fibrin glue produced with either autologous or bovine thrombin and with liposomes embedded in the glue after clotting. The liposomes embedded within the fibrin glue contain biologically active ingredients that would be released over an extended period of time within the body. However, Marx describes a fibrin sealant where the liposomes are embedded only after the coagulation has occurred involving a clotting cascade generated with thrombin and fails to envision utilizing a fibrin sealant that is produced with anything other than thrombin as a clotting agent for the fibrin.

In 1993 researchers from the Center for the Study of Venoms and Venomous Animals—CEVAP of São Paulo State University—UNESP standardized and reported on another type of fibrin glue derived from snake venom (luan, F C., Thomazini I A., Mendes-Giannini M J S., Toscano E., Viterbo F., Moraes R A., Barraviera B., Cola de fibrina derivada de veneno de cobra e processo para sua preparacão. Patente requerida junto ao Instituto Nacional de Propriedade Industrial. *Rev. Propried. Industr.*, 1993, 1165, 27: Viterbo F., Thomazini IA., Giannini M J S M., Reparacão de nervos periféricos corn cola de fibrina derivada de veneno de cobra.

Resultados preliminares. *Acta Cir. Bras.,* 1993, 8, 85). This new glue consists of a cryoprecipitate containing human, bovine, bubaline or equine fibrinogen and a "thrombin-like" fraction of snake venom. This glue is different from the traditional glues since it uses animal instead of human fibrinogen and it also substitutes bovine thrombin for a "thrombin-like" enzyme extracted from Crotalus durissus teffificus venom which was isolated by Raw et al. (Raw I., Rocha M C., Esteves M I., Kamiguti A S., Isolation and characterization of a thrombin-like enzyme from the venom of Crotalus durissus terrificus. *Braz. J. Med. Biol. Res.,* 1986, 19, 333). The "thrombin-like" enzyme is much more potent than bovine thrombin in the conversion of fibrinogen into fibrin (Thomazini-Santos I A., Avaliacão do tempo de coagulacão da trombina bovina, da reptilase e da fracão do "tipo-trombina" de serpentes Crotalus durissus teffificus, empregando-se crioprecipitado de diferentes espécies animais. Botucatu: Universidade Estadual Paulista, Faculdade de Medicina, 1996. 71 p). The utilization of this glue has the advantage of permitting the use of homologous, autologous and heterologous fibrinogen, according to necessity. Applicability of fibrin glue derived from snake venom was subsequently tested and approved for use in different animal tissues.

Viterbo et al. and luan et al., (luan F C., Thomazini I A., Mendes-Giannini M S., Viterbo F., Toscano E., Moraes R A., Barraviera B.; Reparation of peripheral nerves with fibrin glue prepared from snake venom. Preliminary results. *Rev. Paul. Med.,* 1995, 113, 1000-2) tested the fibrin glue derived from snake venom in the repair of sciatic nerve of Wistar rats and observed its good hemostatic and adhesive properties, as well as a satisfactory regeneration of the sealed nerves. Viterbo et al. used bubaline, equine, bovine and human fibrinogen. These authors concluded that fibrin glue derived from snake venom and bubaline fibrinogen showed to be a major alternative for the repair of peripheral nerves.

Leite et al. (Leite C V S., Naresse L E., Saad L H C., Thomazini I A., Barraviera B., Kobayasi S.; Cicatrizacão intestinal—efeito da cola de fibrina derivada de veneno de cobra na anastomose do cólon de ratos. In: *Congresso Brasileiro De Colo-Proctologia,* 43, Recife, 1994. Anais . . . Recife, 1994) tested the fibrin glue derived from snake venom in anastomoses of colon of Wistar rats with good results. The glue they used was made up of snake venom fraction and bubaline fibrinogen.

Stolf et al. (Stolf H O., Barraviera S R C S., Thomazini I A., Giannini M J S M., Toscano E., Barraviera B.; Cola de fibrina derivada de veneno de cobra. Uso experimental em cirurgia dermatológica. In: *Congresso Da Sociedade Brasileira De Dermatologia,* 48, Curitiba, 1993. Anais . . . Curitiba, 1993) evaluated this fibrin glue in skin of rabbits subjected to elliptical skin incision on the trunk. The results obtained suggested that the glue acts efficiently on the healing process due to an increase of a fibrin network.

Subsequently, Edwardson et al., U.S. Pat. No. 5,770,194 described an autologous fibrin sealant composition produced with a thrombin-like enzyme derived from snake venom (Batroxobin) and without the use of any bovine derived additives such as Aprotinin, derived from bovine lung, or thrombin which could carry blood-transmitted infections, infectious agents and viruses pathogenic to mammals. Bovine thrombin has been known to carry the infectious agent bovine spongiform encephalitis (BSE) and other viruses. Furthermore, bovine thrombin is a potent antigen, which can cause immunological reactions in humans. Thus, the use of bovine thrombin could result in the recipient of the bovine thrombin being adversely affected. Additionally, Edwardson et al., U.S. Pat. No. 5,770,194 described a kit comprising autologous fibrin monomer or non-crosslinked fibrin which can be polymerized to form fibrin sealant utilizing a thrombin-like enzyme derived from snake venom thus avoiding concerns for blood-transmitted infections and or viruses that are pathogenic to mammals. The present inventors have observed that Edwardson et al. do not envision the use of supplemented autologous tissue sealants where there is the added benefit of a therapeutic composition which is to be released from the fibrin matrix over a sustained period that is greater than the period which might normally be obtained through standard diffusion kinetics. Additionally, the degradation or resorption rate of fibrin sealants produced from thrombin-like enzymes may be tailored to have different diffusion or resorption rates than fibrin sealants produced with thrombin.

SUMMARY OF THE INVENTION

One mechanism for hemostasis, i.e., prevention of blood loss, of a mammal is the formation of a blood clot. Clot formation in humans, i.e., blood coagulation, occurs by means of a complex cascade of reactions with the final steps being the conversion of fibrinogen—a monomer—by thrombin, calcium ions and activated factor XIII to form ultimately crosslinked fibrin II polymer, which is the fibrin clot.

The formation of crosslinked fibrin II polymer proceeds by the fibrinogen being converted by thrombin to fibrin I monomer, which spontaneously polymerizes to form fibrin I polymer, which is sometimes referred to as soluble fibrin I because by treatment by appropriate chemical means the fibrin I polymer can be reconverted to fibrin I monomer. The fibrin I polymer is then converted by thrombin to fibrin II polymer, which is sometimes referred to as soluble fibrin II because by treatment by appropriate chemical means the fibrin II polymer can be converted to fibrin II monomer. The fibrin II polymer, under the influence of factor XIIIa—known as activated factor XIII—is then crosslinked to form crosslinked fibrin II, which is the fibrin clot. Factor XIII is activated by thrombin in the presence of calcium ions. Cross-linked fibrin II is sometimes referred to as insoluble fibrin II because it cannot be converted to fibrin II monomer.

It should be noted that thrombin is formed from prothrombin. Prothrombin is converted to thrombin by factor Xa in the presence of calcium and other ancillary substances.

Fibrinogen represents about 2 to 4 grams/liter of the blood plasma protein. Fibrinogen is a monomer that consists of three pairs of disulfide-linked polypeptide chains designated $(A.alpha.)_2$, $(B.beta.)_2$, $.gamma._2$. "A" and "B" represent the two small aminoterminal peptides, known as fibrinopeptide A and fibrinopeptide B, respectively. The cleavage of fibrinopeptides A from fibrinogen in the transformation of fibrinogen by thrombin results in the fibrin I compound and the subsequent cleavage of fibrinopeptides B results in the fibrin II compound. Such cleavage of fibrinopeptides A and B reduces the molecular weight of fibrinogen by an extremely small amount, about 6,000 out of 340,000 daltons, but exposes the polymerization sites.

A fibrin sealant is a biological adhesive whose effect imitates the final stages of coagulation, thereby resulting in a fibrin clot. Conventional fibrin sealants consist of concentrated human fibrinogen, bovine aprotinin and factor XIII, as the first component and bovine thrombin and calcium chloride as the second component. Application is generally carried out with a double-barreled syringe, which permits simultaneous application of both components to the site where one wants to form the fibrin clot. Aprotinin is a fibrinolytic inhibitor added to promote stability of fibrin sealants.

The fibrinogen component of the fibrin sealant is prepared from pooled human plasma. The fibrinogen can be concentrated from the human plasma by cryoprecipitation and precipitation using various reagents, e.g., polyethylene glycol, ether, ethanol, ammonium sulfate or glycine.

Recently, there has also been a renewed interest in the preparation of fibrin sealants that utilize autologous fibrin. An autologous fibrin sealant is a fibrin sealant wherein the fibrinogen component of the fibrin sealant is extracted from the patient's own blood. The use of an autologous fibrin sealant is preferred because it eliminates the risk of transmission of blood-transmitted infections, e.g., hepatitis B, non A, non B hepatitis and acquired immune deficiency syndrome (AIDS), that could otherwise be present in the fibrinogen component extracted from pooled human plasma. Autologous fibrin sealant has not been used in practice because it has been time consuming to obtain and because the results, in contrast to pooled human-derived fibrinogen, have been inconsistent.

Also, there are some risks attendant to use of current pooled human-derived fibrin sealant products. For example, an infection can be transmitted by a fibrin sealant not only by means of the fibrinogen but also by means of the bovine aprotinin and the bovine thrombin component. Bovine thrombin has been known to carry the infectious agent bovine spongiform encephalitis (BSE) and other viruses pathogenic to mammals. Furthermore, bovine thrombin is a potent antigen, which can cause immunological reactions in humans. Thus, the use of bovine thrombin could result in the recipient of the bovine thrombin being adversely affected.

The present inventors have recognized that autologous fibrin sealant would be particularly advantageous if it included a supplement (a therapeutic agent) which could be provided to a patient at a point in the body so that the supplement would be slowly released over time at the point of need, such as an injured disc in a human spine.

Furthermore, the inventors herein have determined that not only is there a need for a fibrin sealant that can be delivered to a patient without the risk of viral contamination or other adverse affects, but for a fibrin sealant that includes a supplement to provide a desired therapeutic effect.

The present invention provides a solution to one or more of the disadvantages and problems described above.

The disclosure herein generally relates to an invention and method for the preparation and use of novel enhanced autologous biological tissue adhesives prepared in the absence of externally supplied thrombin. More particularly, the present invention relates to a method of preparing an autologous fibrin sealant having been formed with a thrombin-like (non-thrombin) enzyme and whereby said sealant is augmented with various biological and non-biological agents. The invention further relates to a novel method of using said enhanced autologous fibrin sealant whereby the sealant and accompanying agent are delivered directly to a site within the body and sealed in place due to the bio-static quality of the autologous sealant resulting in enhanced therapeutic value, derived for example by the prolonged presence of said accompanying agent at the sight. The autologous nature of the fibrin sealant, prepared from fibrinogen extracted from the patient's own blood, in the absence of (human or bovine-derived) thrombin, eliminates the risk of transmission of blood-transmitted infections, infectious agents and viruses pathogenic to mammals. Furthermore, the absence of bovine thrombin or other bovine derived additives, from the enhanced autologous fibrin sealant eliminates the added risk of immunological reactions which are known to be caused in some humans from bovine antigen.

The present invention is directed to compositions of enhanced autologous fibrin sealants, their preparation and methods for use thereof.

In one broad respect, this invention is a composition useful for preparing a tissue sealant for use on a patient, comprising: autologous fibrinogen, an activating agent and at least one supplement.

In another broad respect, this invention is a method of treating tissue of a patient wherein the tissue has at least one defect, comprising: applying a composition to the tissue, wherein the composition comprises autologous fibrinogen and an activating agent, and wherein the composition forms fibrin.

In another broad respect, this invention is a method of treating a human spinal disc having at least one defect, comprising: introducing a composition into the disc, wherein the composition comprises autologous fibrinogen and an activating agent, and wherein the composition forms fibrin.

In another broad respect, the present invention provides a composition of matter that promotes the localized delivery of an x-ray contrast medium, a substance that is opaque to x-rays; when administered it allows a radiologist to examine the organ or tissue it fills, and an autologous tissue sealant.

In another embodiment, the present invention provides a composition of matter that promotes the localized delivery of an x-ray contrast medium, a therapeutic amount of the patients own blood (sometimes referred to as a "blood patch" and an autologous tissue sealant.

In another embodiment, the present invention provides a composition of matter that promotes the localized delivery of at least one drug, comprising: an autologous tissue sealant; and at least one drug. It should be appreciated that the material that forms the fibrin, and not the enzyme that promotes formation of fibrin, is autologous.

In another embodiment, the present invention provides a composition of matter that promotes the localized delivery of at least one growth factor, comprising: an autologous tissue sealant; and at least one growth factor.

In another embodiment, the present invention provides a process for promoting the healing of wounds, comprising applying to the wound, a composition that contains an autologous tissue sealant and an effective concentration of at least one growth factor, wherein the concentration is effective to promote wound healing.

In another embodiment, the present invention provides a process for promoting the healing of cartilage defects, comprising applying to the wound, a composition that contains an autologous tissue sealant and an effective concentration of cells that could produce cartilage, wherein the concentration is effective to promote healing.

In another embodiment, the present invention provides a process for promoting the healing of spinal disc fissures, comprising applying into and around the spinal disc, a composition that contains an autologous tissue sealant to seal the disc fissure and an effective concentration of at least one drug to reduce inflammation, wherein the concentration is effective to promote healing.

In another embodiment, the composition may be supplemented with, for example, one or more analgesics, anesthetics, antimicrobial compounds, antibiotics, antifibrinolytic agents, anti-inflammatory compounds, antibodies, anticoagulants, antifungal compounds, antiangiogenins, antiseptics, cardiovascular drugs, cytokines, cytotoxins or cell proliferation inhibiting compounds, chemotherapeutic drugs, interferons, growth factors, hormones, lipids or liposomes, oligonucleotides or polynucleotides, osteoinducers, cartilage-inducing compounds, polymers, polysaccharides, proteoglycans, polypeptides, protease inhibitors, steroids, vasoconstrictors, vasodilators, vitamins, nutritional supplements, minerals, stabilizers and combinations thereof.

In another embodiment, this invention provides a method of treating injured, disrupted, damaged, degenerated or wounded tissue in a patient by applying enhanced, thrombin-like enzyme activated, autologous tissue sealants to said tissue in a pressurized fashion.

While in a further embodiment, this invention provides a method of treating injured, disrupted, damaged, degenerated or wounded joints in a patient by applying enhanced, thrombin-like enzyme activated, autologous tissue sealants to said tissue in a pressurized fashion.

The subject invention relates to a method for utilizing a fibrin sealant which comprises: (a) contacting a desired site with a composition comprising fibrin monomer and a supplement; and (b) converting said fibrin monomer to a fibrin polymer concurrently with said contacting step, thereby forming a fibrin clot that contains the supplement.

The subject invention also provides methods for preparing such composition and compositions and kits comprising such fibrin monomer and supplement.

Another aspect of the subject invention relates to a method for utilizing a fibrin sealant which comprises: (a) contacting a desired site with a composition comprising noncrosslinked fibrin; and (b) converting said noncrosslinked fibrin to crosslinked fibrin concurrently with said contacting step, thereby forming a fibrin clot.

The subject invention also provides methods for preparing such a composition and compositions and kits comprising such noncrosslinked fibrin.

DETAILED DESCRIPTION OF THE INVENTION

The compositions, method, and steps of the present invention are now described in more detail.

As used herein, a "supplement" is a drug or therapeutic agent. The supplement is used in a therapeutically effective amount as would be apparent to one of skill in the art based on the choice of supplement(s), desired effect, amount of fibrin sealant, location within the body for treatment, and so on. The drugs and therapeutic agents that can be employed in the practice of this invention include analgesics, anesthetics, antimicrobial compounds, antibiotics, antifibrinolytic agents, anti-inflammatory compounds, antibodies, anticoagulants, antifungal compounds, antiangiogenins, antiseptics, cardiovascular drugs, cytokines, cytotoxins or cell proliferation inhibiting compounds, chemotherapeutic drugs, interferons, growth factors, hormones, lipids or liposomes, oligonucleotides or polynucleotides, osteoinducers, cartilage-inducing compounds, polymers, polysaccharides, proteoglycans, polypeptides, protease inhibitors, steroids, vasoconstrictors, vasodilators, vitamins, nutritional supplements, minerals and stabilizers. One or more supplements can be used for a given fibrin sealant.

In the practice of this invention, fibrin monomer or a composition comprising noncrosslinked fibrin is utilized as a component of to form the fibrin sealant.

As used herein "activating agent" means a compound that reacts with fibrinogen to form fibrin. Representative examples of such activating agents include but are not limited to thrombin and enzymes derived from snake venom or arachnid venom. As used herein, activating agent and thrombin-like enzyme have the same meaning.

As used herein "fibrin" means any form of fibrin. Nonlimiting examples of fibrin include fibrin I, fibrin II and des BB fibrin. The fibrin can be in monomeric form or polymeric form, wherein the polymeric form is either noncrosslinked or crosslinked.

As used herein "Fibrin monomer" includes any form of fibrin, e.g., fibrin I, fibrin II or des BB fibrin, wherein the fibrin is in monomeric form or oligomeric form that can be solubilized in the composition comprising fibrin monomer and wherein the fibrin monomer can be converted to fibrin polymer.

As used herein "Fibrin Polymer" includes any form of fibrin, e.g., fibrin I, fibrin II or des BB fibrin, wherein said fibrin is in polymeric form, either noncrosslinked or crosslinked.

As used herein "Noncrosslinked fibrin" includes any form of fibrin, e.g., fibrin I, fibrin II or des BB fibrin, wherein said fibrin is noncrosslinked and can be converted to crosslinked fibrin. The noncrosslinked fibrin can be fibrin monomer or noncrosslinked fibrin polymer.

As used herein "Crosslinked fibrin" includes any form of fibrin, e.g., fibrin I, fibrin II or des BB, wherein the fibrin is a fibrin polymer that is crosslinked.

The Composition Comprising Fibrin Monomer

The fibrin composition of the subject invention comprising fibrin monomer is a composition that contains any form of fibrin monomer that can be converted to fibrin polymer. Nonlimiting examples of fibrin monomer include fibrin I monomer, fibrin II monomer or des BB fibrin monomer, with fibrin I monomer being preferred. Of course, mixtures of the fibrin monomer can be present. Also, for the purpose of the subject invention, fibrin polymer includes any polymer resulting from the polymerization of fibrin monomer. Thus, for example, the conversion of fibrin I monomer to fibrin polymer can result in fibrin I polymer, crosslinked or noncrosslinked, and/or fibrin II polymer, crosslinked or noncrosslinked, depending on how the conversion step is carried out.

Fibrin I monomer is preferred because it can, in contrast to fibrinogen, readily be converted to fibrin polymer without the use of thrombin or factor XIII. In fact, the fibrin I monomer can spontaneously form fibrin I polymer, which can act as the fibrin clot, regardless of whether the fibrin I polymer is crosslinked or noncrosslinked or further converted to fibrin II polymer. Thus, since the formation of the fibrin I polymer from fibrin I monomer is spontaneous, the fibrin I polymer can be formed without thrombin and factor XIII, thereby avoiding the problems associated with bovine thrombin. It should be noted that if fibrin I monomer is utilized such that the fibrin I monomer comes into contact with patient's blood, for example, on a wound, the patient's thrombin and factor XIII may convert the fibrin I polymer to crosslinked fibrin II polymer.

The Composition Comprising Noncrosslinked Fibrin

The composition comprising noncrosslinked fibrin is a composition that contains any form of noncrosslinked fibrin. Nonlimiting examples of noncrosslinked fibrin are noncrosslinked fibrin I, noncrosslinked fibrin II and des BB fibrin, with noncrosslinked fibrin I being preferred. Of course, mixtures of noncrosslinked fibrin can be present. Also, for the purpose of the subject invention "crosslinked fibrin" includes any form of fibrin resulting from the conversion of noncrosslinked fibrin to crosslinked fibrin. Thus, the crosslinked fibrin, for example, resulting from the conversion of noncrosslinked fibrin I to crosslinked fibrin, can be crosslinked fibrin I and/or crosslinked fibrin II, depending on how the conversion step is carried out.

Noncrosslinked fibrin I is preferred because it can more readily, as compared to fibrinogen, be converted to crosslinked fibrin. In fact, it is believed that fibrin I can form crosslinked fibrin I, which can act as the fibrin sealant. Thus, the formation of the crosslinked fibrin I from noncrosslinked fibrin I can be carried out without thrombin, thereby avoiding the problems associated with bovine thrombin, albeit activated factor XIII may be required. (It should be noted that if noncrosslinked fibrin I is utilized such that the noncrosslinked fibrin I comes into contact with patient's blood, for example, on a wound, the patient's thrombin and factor XIII may convert the fibrin I to crosslinked fibrin II.)

Also, the noncrosslinked fibrin can be a polymer, oligomer or monomer, albeit an oligomer or monomer is preferred, i.e., fibrin monomer. This is due to the fact that noncrosslinked fibrin in polymeric form is generally a gel and, therefore, is very difficult to deliver to the desired site and provides for less intimate contact with cells at the desired site. In contrast, a resulting noncrosslinked fibrin in oligomeric or monomeric form is soluble and, therefore, can more readily be delivered to the desired site and have more intimate contact with the cells. Of course, the composition can contain a mixture of such forms of noncrosslinked fibrin.

The Source of the Composition Comprising Fibrin Monomer or Noncrosslinked Fibrin The source of the composition comprising fibrin monomer or noncrosslinked fibrin can be any source known or to be developed so long as the fibrin monomer can be converted to fibrin polymer or the noncrosslinked fibrin can be converted to crosslinked fibrin. Nonlimiting sources of compositions comprising fibrin monomer or noncrosslinked fibrin are blood, preferably mammalian blood and even more preferably human blood, cell cultures that secrete fibrinogen and recombinant fibrinogen, with blood being preferred. Blood can be any form of blood including, for example, whole blood or prepared fibrinogen preparations. Also, blood can be utilized to prepare an autologous fibrin sealant.

It is believed that a composition comprising noncrosslinked fibrin I, either as fibrin I monomer or fibrin I polymer, prepared from whole blood as described below can be converted to crosslinked fibrin II without the addition of thrombin, factor XIII and other necessary substances for blood coagulation. It is believed that this is due to the fact that the composition comprising noncrosslinked fibrin I prepared from whole blood retains sufficient quantities of prothrombin, factor XIII and such other necessary substances from the plasma such that the noncrosslinked fibrin I can be converted to crosslinked fibrin II without the addition of exogeneous thrombin and factor XIII. This endogenous prothrombin and factor XIII can be utilized in the fibrin sealant of the subject invention as components of the composition comprising fibrin monomer or noncrosslinked fibrin.

However, it should be noted that sufficient quantities of this endogenous thrombin and factor XIII are not retained so as to convert fibrinogen to crosslinked fibrin II at a reaction rate that is suitable for a fibrin sealant. It is believed that more thrombin is required to convert fibrinogen to crosslinked fibrin II than to convert noncrosslinked fibrin I to crosslinked fibrin II at an equivalent reaction rate.

Each one of such three sources contains fibrinogen, which can be converted to the fibrin monomer or noncrosslinked fibrin. In addition to such conversion step, the resultant composition that contains the fibrin monomer or noncrosslinked fibrin should be in a concentrated form. It is preferred that the concentration of the fibrin monomer be no less than about 10 mg/ml, more preferably from about 20 mg/ml to about 200 mg/ml, even more preferably from about 20 mg/ml to about 100 mg/ml and most preferably from about 25 mg/ml to about 50 mg/ml.

In addition, it is preferred that the fibrin monomer or noncrosslinked fibrin be nondynamic. For the purpose of the present invention a nondynamic composition comprising noncrosslinked fibrin means that the noncrosslinked fibrin in such composition does not crosslink for at least about 1.5 minutes, preferably for at least about 3 minutes and more preferably for at least about 30 minutes after preparation of such composition. For the purpose of the present invention a nondynamic composition comprising fibrin monomer means that the fibrin monomer in such composition does not polymerize for at least about 1.5 minutes, preferably for at least about 3 minutes, more preferably for at least about 30 minutes and even more preferably at least about 2 hours after the preparation of the composition. In fact, it should be noted that the composition comprising fibrin monomer can be nondynamic for at least several days, i.e., about 72 hours, after its preparation.

Preparation and Concentration of a Composition Comprising Fibrin Monomer or Noncrosslinked Fibrin from Blood The composition comprising fibrin monomer or noncrosslinked fibrin can be prepared from blood. The method can result in a hydrogen bonded fibrin polymer, which is a form of noncrosslinked fibrin. Such polymer can then be utilized as a component of the fibrin sealant or be converted to fibrin monomer by a process referred to as solubilization, all as described hereinbelow. Also, it is preferred that the composition comprising fibrin monomer or noncrosslinked fibrin be prepared in a sterile environment.

Compositions comprising fibrin monomer or noncrosslinked fibrin can be prepared from whole blood by withdrawing blood from a donor and preferably in the presence of an anticoagulant. Any anticoagulant can be utilized. Nonlimiting examples of anticoagulants are heparin, EDTA, hirudin, citrate or any other agent that can, directly or indirectly, prevent the formation of thrombin, with citrate being preferred.

The plasma, which contains the fibrinogen, is then separated from the whole blood. Any separation technique can be utilized, for example, sedimentation, centrifugation or filtration. Centrifugation can be carried out at about 3,000 g. for about 10 minutes. However, if it is desired to obtain plasma rich in platelets, centrifugation can be carried out at lower g force, e.g., 500 g for about 20 minutes. The supernatant, which contains the plasma, can be removed by standard techniques.

Filtration can be carried out by passing the whole blood through a suitable filter that separates blood cells from plasma. It is preferred that the filter be a microporous membrane exhibiting good protein transmission.

The resultant plasma is then treated to convert the fibrinogen to fibrin monomer or noncrosslinked fibrin. This conversion can be carried out by any technique that-is known or to be developed.

A preferred technique to produce fibrin monomer or noncrosslinked fibrin is by means of a thrombin-like enzyme, which includes thrombin. A thrombin-like enzyme is any enzyme that can catalyze the formation of fibrin from fibrinogen. A common source of activating agent (the thrombin-like enzyme) is a snake venom. Preferably, the thrombin-like enzyme is purified from the snake venom. Depending on the choice of thrombin-like enzyme, such thrombin-like enzyme can release fibrinopeptide A—which forms fibrin I—fibrinopeptide B—which forms des BB fibrin—or both fibrinopeptide A and B—which forms fibrin II. It should be noted that those activating agents that release fibrinopeptide A and B may do so at different rates. Thus, the resultant composition could be, for example, a mixture of fibrin II and fibrin I or a mixture of fibrin II and des BB fibrin.

TABLE I is a nonlimiting list of the sources of the snake venoms that can be utilized in the subject invention, the name of the thrombin-like enzyme and which fibrinopeptide(s) is released by treatment with the enzyme.

TABLE 1

| SOURCE | NAME | FIBRINOPEPTIDE RELEASED |
|---|---|---|
| *Agkistrodon acutus* | Acutin | A |
| *A. contortrix contortrix* | Venzyme | B, (A)* |
| *A. halys Pallas* | | B, (A)* |
| *A. (Calloselasma) rhodostoma* | Ancrod, Arvin | A |
| *Bothrops asper* | (B. Asperase atrax) | A |
| *B. Atrox* | Batroxobin, Reptilase Reagent | A |
| *B. insularis* | | A, B |
| *B. jararaca* | Botropase | A |
| *B. Moojeni (B. Atrox)* | Batroxobin, Defibrase | A |
| *Lachesis muta muta* | | A, B |
| *Crotalus adamanteus* | Crotalase | A |
| *C. durissus terrificus* | | A |
| *Trimeresurus flavoviridis* | Flavoxobin | A |
| *T. gramineus* | | A |
| *Bitis gabonica* | Gabonase | A, B |

*( ) means low activity.

For a review of thrombin-like enzymes from snake venoms, see H. Pirkle and K. Stocker, Thrombosis and Haemostasis, 65(4):444-450 (1991).

The preferred thrombin-like enzymes are Batroxobin, especially from B. Moojeni, B. Maranhao and B. atrox and Ancrod, especially from A. rhodostoma.

The fibrin monomer or noncrosslinked fibrin can be prepared by contacting the plasma with the thrombin-like enzyme, thereby permitting the fibrinogen in the plasma to be converted to a fibrin monomer. However, the resultant fibrin monomer spontaneously polymerizes to form a hydrogen bonded polymer in the form of a gel, which separates from the remaining serum, which is a solution. The gel is a form of the composition comprising noncrosslinked fibrin.

This noncrosslinked fibrin gel can be harvested by, for example, centrifugation (3,000 g. for 10 minutes), direct manual separation of the noncrosslinked fibrin from the serum, filtration, directly or under pressure, followed by the removal of the separated serum. (A 1-100 micron pore size filter can be utilized, for example, a sintered polypropylene 20 micron pore size filter from Porex, Inc., a teflon 20-70 micron pore size filter from Fluorotechniques, Inc. or a nylon 66 22-46 micron pore size filter from Costar, Inc.).

This harvestation separates the noncrosslinked fibrin gel from serum, which is a solution, and, thereby, concentrates the noncrosslinked fibrin gel vis-à-vis the plasma. It should be noted that the noncrosslinked fibrin gel retains at least some prothrombin, factor XIII, and such other necessary substances from the plasma such that the noncrosslinked fibrin I can be converted to crosslinked fibrin II without the addition of exogenous thrombin or factor XIII. This endogenous prothrombin and factor XIII can be utilized in the fibrin sealant of the subject invention as components of the composition comprising fibrin monomer or noncrosslinked fibrin.

The force of centrifugation or pressure of filtration during harvestation will determine how much of the serum is removed from the noncrosslinked fibrin gel, with the higher such force or pressure, the more concentrated the resulting noncrosslinked fibrin gel. However, it is preferred that such force or pressure not be so great that the prothrombin and factor XIII are removed from the noncrosslinked fibrin gel.

The noncrosslinked fibrin gel is now ready for use as a component of the fibrin sealant as a form of the composition comprising noncrosslinked fibrin. It has been observed that when such composition is prepared from whole blood, from about 60% to about 90% of the original fibrinogen is present in the composition, but, of course, in the form of a noncrosslinked fibrin.

The composition comprising the noncrosslinked fibrin can be utilized immediately after it is prepared. In fact, it is particularly preferred to utilize such composition immediately after its preparation when the composition is autologous. If the composition is not utilized immediately after its preparation, the composition can be stored. Storage of the composition requires that the composition be preserved by, for example, freezing or lyophilizing the composition or holding the composition at 4 degrees C. The composition in frozen or lyophilized form will be stable for a period of months. When the composition is held at 4 degrees C., it is believed that the composition is stable for at least a period of days.

If the composition is frozen, the composition must be thawed prior to the time of use.

This technique that results in the formation of the noncrosslinked fibrin gel converts the fibrinogen to the noncrosslinked fibrin gel and concentrates such gel in essentially one step. Alternatively, and less preferred, one can concentrate fibrinogen by conventional techniques, e.g., cryoprecipitation and precipitation using various reagents, e.g., polyethylene glycol, ether, ethanol, ammonium sulfate or glycine. The concentrated fibrinogen can then be converted to the noncrosslinked fibrin gel by the techniques described above or, preferably, since the fibrinogen is already concentrated, then the fibrinogen can be converted to a composition comprising fibrin monomer without the need to first form the noncrosslinked fibrin gel. This can be carried out by contacting the concentrated fibrinogen with a chaotropic agent to obtain a fibrinogen solution.

The chaotropic agent is necessary to prevent the fibrin monomer, which is formed upon contact of the fibrinogen with the thrombin-like enzyme, from spontaneously polymerizing. The chaotropic agent is mixed with such fibrinogen composition and then agitated for about 1 to 2 minutes to form the fibrinogen solution. The fibrinogen can then be converted to a fibrin monomer by, for example, a thrombin-like enzyme, as described above, or by a thrombin-like enzyme immobilized on a support, as described below.

Suitable chaotropic agents include urea, sodium bromide, guanidine hydrochloride, KCNS, potassium iodide and potassium bromide. The preferred concentration of the chaotropic agent is from about 0.2 to about 6.0 molar and most preferably from about 0.3 to about 2.0 molar. It is preferred to utilize the least amount of chaotropic agent possible that still prevents the fibrin monomer from spontaneously polymerizing.

It should be noted that it is preferred that a source of calcium ions not be added to the chaotropic agent until it is desired to convert the fibrin monomer to fibrin polymer, as described below. This ensures that the fibrin monomer will not crosslink due to activation of any endogenous blood coagulation factors.

Immobilization of Thrombin-Like Enzyme on a Support

In one embodiment, the thrombin-like enzyme is immobilized on a support. This permits one to readily separate the immobilized enzyme from the plasma, thereby preventing the composition comprising noncrosslinked fibrin from being contaminated by the enzyme.

Any support to which the thrombin-like enzyme can be attached can be utilized in the subject invention. Nonlimiting examples of suitable supports are cellulose, polydextrans, agarose, polystyrenes, silica, polyacrylic acids, polyacrylamides, polyvinylalcohols, glass beads, polytetrafluorethylene, polycarbonate, collagen, cellulose derivatives, teflon and their composites, with silica polystyrene and agarose being preferred and agarose being most preferred.

In another embodiment the thrombin-like enzyme is attached to a support that is a filter or on one side of the filter and attached to another support, e.g., a bead. Otherwise, the thrombin-like enzyme will pass through the filter. Thus, the pore size of the filter should be such that the immobilized thrombin-like enzyme cannot pass through the filter, but the noncrosslinked fibrin can pass through the filter. The noncrosslinked fibrin is prepared by contacting the plasma with the thrombin-like enzyme on one side of the filter to form a fibrin monomer, which, along with the rest of the plasma, passes through the filter. Thus, the resulting composition comprising noncrosslinked fibrin is necessarily separated from the thrombin-like enzyme. The fibrin monomer, after passage through the filter, spontaneously polymerizes to form a noncrosslinked fibrin polymer.

In order to immobilize the thrombin-like enzyme to a support, the support must be activated. This can be carried out by any suitable technique. For example, various activation chemistries available for derivatizing supports are: diazonium groups, isocyanate groups, acid chloride groups, acid anhydride groups, sulphonyl chloride groups, dinitro fluorophenyl groups, isothiocyanate groups, hydroxyl groups, amino groups, n-hydroxysuccinimide groups, triazine groups, hydrazino groups, carbodiimide groups, silane groups and cyanogen bromide.

The preferred activation chemistry is by means of a hydrazide group. The use of a hydrazide activated support results in a maximal percentage (at least about 30% to about 50% as measured by the S2238 assay of the thrombin-like enzyme retaining its activity with essentially no enzyme leaching. Also, low pH values, e.g., pH 4-6, can be utilized for enzyme coupling to prevent enzyme degradation.

Generally, the support is activated by a highly reactive compound, which subsequently reacts with a functional group of a ligand, e.g., —OH, —NH2, —SH, —COOH, —CHO to form a covalent linkage. The preferred activation chemistries for use in the subject invention are:

(a) by means of a triazine group and preferably triazine halogenide groups;
(b) by means of a tresyl chloride group;
(c) by means of a carbonyldiimidazole group;
(d) by means of a cyanogen bromide group; and
(e) by means of a hydrazide or amino group.

In (a)-(d), the protein is coupled via reaction with —NH$_2$, —SH, or —OH groups, whereas in (e), the protein is coupled via an oxidized carbohydrate moiety, i.e., —CHO. The use of these chemistries results in a maximal percentage (at least about 30% to about 50% as measured by the S2238 assay) of the thrombin-like enzyme retaining its activity with essentially no enzyme leaching.

For triazine activation two different methods were used. The first method involved linking the triazine ring directly to surface OH groups. This is similar to the CNBr activation method employed, where surface diol groups were reacted with CNBr. For triazine activation, OH groups of agarose were reacted with triazine (cyanuric chloride).

Generally, the support is activated by a highly reactive compound, which subsequently reacts with a functional group of the ligand, e.g., —OH, —NH$_2$, —SH, —CHO, to form a covalent linkage. Remaining active groups, which have no thrombin-like enzyme attached, can be, but it is not essential, blocked with non-reactive compounds such as ethanolamine, acetic anhydride or glycine.

The preferred activation chemistries for use in the subject invention are:

(a) Cyanogen bromide activation followed by direct coupling of enzyme via —NH$_2$ groups on the protein.

(b) Activation of the support with monochlorotriazine followed by coupling of an enzyme via —NH$_2$, —OH or —SH groups.

(c) Activation of the support with dichlorotriazine followed by coupling of the enzyme via —NH$_2$, —OH or —SH groups.

(d) Tresyl chloride activation of the support followed by coupling of the enzyme via —NH$_2$, —OH or —SH.

(e) Activation of the support with adipic acid hydrazide or hydrazine followed by coupling of oxidized enzyme via —CHO groups.

(f) Activation of the support with an amino ligand followed by coupling of oxidized enzyme via —CHO groups.

All the above preferred methodologies employ agarose as the support, however, it is possible to use silica. When using this support, the preferred activation chemistries are:

(a) Gamma—glycidoxypropyltrimethoxysilane activation with direct coupling of the thrombin-like enzyme via —NH$_2$ groups on the protein.

(b) Cyanogen bromide activation followed by direct coupling of enzyme via —NH$_2$ groups on the protein.

(c) Gamma—glycidoxytrimethoxysilane activation followed by opening of the epoxide ring to form a diol group, which can be subsequently activated with cyanogen bromide. Direct coupling of the enzyme can be achieved via —NH2 groups on the protein.

(d) Gamma—glycidoxypropyltrimethoxysilane activation followed by preparation of amino-silica by treatment with ammonia solution.

The amino-silica can be subsequently activated with cyanuric chloride (triazine) and the enzyme coupled via —NH$_2$, —OH or —SH groups.

Coupling of Enzyme to Activated Support

Coupling of the enzyme to the activated support must be buffered at a certain pH to obtain optimal enzyme binding. Generally, with standard activation techniques such as gamma-glycidoxy-propyltri-methoxysilane coupling of enzyme to activated support and cyanogen bromide coupling of any protein to active groups requires buffering at a pH 1-2 units higher than the pKa of the primary and secondary amines of the enzyme. However, the use of cyanuric chloride as the activator enables the use of much lower pH buffers (optimal coupling pH is 4-6). Another method of coupling glycoproteins such as batroxobin to an inert support is via their carbohydrate moieties. This involves first the oxidation of the sugar group to —CHO groups followed by direct coupling at acid pH to an amino group such as hydrazide. A wide range of coupling buffers can be used. See, for example, Table 2;

TABLE 2

EXAMPLES OF COUPLING BUFFERS USED IN ENZYME IMMOBILIZATION TO SILICA AND AGAROSE SUPPORTS

| SUPPORT | ACTIVATION METHOD | COUPLING BUFFER |
|---|---|---|
| Silica | Gamma-glycidoxypropyl-trimethoxysilane | 0.1M Sodium bicarbonate pH 8-9 10 mM HEPES pH 7.0 |
| Silica | Gamma-glycidoxypropyl-trimethoxysilane + cyanogen bromide | 0.1M Sodium bicarbonate pH 8-9 10 mM HEPES pH 7.0 |
| Silica | Cyanogen Bromide | Water pH 7.0 0.1M Sodium bicarbonate pH 7-9 10 mM HEPES pH 7.0 |
| Agarose | Monochlorotriazine | 50 mM Sodium Acetate/1M NaCl pH 4.0 |
| Agarose | Dichlorotriazine | 0.1M Potassium phosphate/1M NaCl pH 8.0-9.0 |
| Agarose | Tresyl chloride | 50 mM Potassium phosphate/0.5M NaCl pH 7.7 |
| Agarose | Hydrazide | 50 mM Sodium Acetate pH 5.5 10 mM NaBH4 |
| Agarose | Amine | 50 mM Sodium Acetate pH 5.5 10 mM NaBH4 |

Blocking and Deactivating Remaining Active Groups

After activation the support will possess more active sites than required for enzyme coupling. These sites, if not deactivated, may covalently bind contaminating proteins, which might affect the biological function of the immobilized enzyme.

Excess groups can be deactivated by the covalent coupling of small, noninterfering amines such as ethanolamine.

If hydrazide or amino activated supports are employed, blocking of residual reactive groups following enzyme coupling can be achieved by use of acetic anhydride.

Depending on the method of immobilization and the support, enzyme inactivation occurs during the immobilization process. Employing a silica support with the most desirable activation chemistry (e.g., cyanogen bromide), up to 80-90% of enzyme activity is lost. However, the use of agarose as the support with cyanuric chloride activation results in less loss of enzyme activity.

Characterization

In order to characterize the efficacy of the immobilized enzyme on the support, two methods can be utilized to assess the amount of active enzyme immobilized on the support; the Clot Time Assay—Clauss A., Acta Haematol., 17:237 (1957) and the S2238 Assay—See Axelsson G. et al., Thromb. Haemost., 36:517 (1976).

To assess the leaching of the enzyme from the support, the following assay can be utilized.

Leaching can be assayed by radiolabelling the thrombin-like enzyme, e.g., $I^{125}$ batroxobin. However, prior to carrying out the leaching assay, it is necessary to remove any unbound radiolabel. This can be achieved by sequentially washing the support with: 50 ml 50 mM sodium acetate pH 5.5, 100 ml 50 mM glycine/1M sodium chloride pH 3.0, 100 ml 50 mM sodium carbonate/1M sodium chloride pH 10.0, 100 ml 50 mM sodium phosphate/1M sodium chloride pH 7.0, 100 ml water and 100 ml 50 mM sodium phosphate/1M sodium chloride pH 7.0.

Formation of Noncrosslinked Fibrin (a) Amount of Enzyme Required

The amount of enzyme required for the treatment of 30-70 ml plasma (obtained from 60-150 ml whole blood) is typically 30-200 units after about 10-15 minutes mixing.

If agarose is employed as the support matrix, 30-200 U of batroxobin results in the formation of noncrosslinked fibrin in about 7-20 minutes. This system employs hydrazide activation and 0.25 g-1.0 g of dry agarose. In this case no blocking of remaining active groups is required.

(b) Reaction of Immobilized Enzyme with Plasma Fibrinogen

Generally, the reaction of the immobilized enzyme with fibrinogen in plasma is performed as follows: approximately 30-70 ml of plasma is added to a known quantity of a dried support, which contains the immobilized thrombin-like enzyme. The suspension is mixed gently (rotation on a spiral mixer or hand mixing) for approximately 7-20 minutes. During this time fibrinogen in the plasma is cleaved by the immobilized enzyme to release fibrinopeptide A and/or fibrinopeptide B resulting in the formation of a hydrogen bonded fibrin I polymer, hydrogen bonded des BB fibrin polymer or hydrogen bonded fibrin II polymer wherein each polymer is associated with the immobilized enzyme.

As described above, the hydrogen bonded fibrin polymer is in the form of a gel and can be harvested by, for example, centrifugation (3,000 g. for 10 minutes) or filtration (through a 1-50 micron membrane filter). Such harvestation separates the hydrogen bonded fibrin polymer from serum and, thereby, concentrates the polymer.

The Prevention of Formation of Crosslinked Fibrin

It should be noted that if a thrombin-like enzyme is utilized in plasma that results in the activation of factor XIII, then it is preferred that the plasma composition be modified at the time the thrombin-like enzyme is utilized so as to prevent the noncrosslinked fibrin, e.g., noncrosslinked fibrin I or II, from forming crosslinked fibrin, e.g., crosslinked fibrin I or II. Of course, it may not be necessary to modify the plasma composition if such composition is utilized as a fibrin sealant immediately after the fibrinogen has been converted to noncrosslinked fibrin.

The plasma composition can be modified to prevent the crosslinking of the noncrosslinked fibrin by any technique that is known or to be developed. This can be carried out-by blocking the endogenous thrombin that can activate the factor XIII, e.g., hirudin or thrombin inhibitors, or blocking the action of activated factor XIII, e.g., by means of heavy metals (Hg), thiomerosal or inhibitory antibodies. Crosslinking of fibrin I or II requires the presence of calcium ions. Thus, if the calcium is removed from the plasma composition, crosslinking of the fibrin I or II can be inhibited. Calcium chelators can be added to the composition to prevent the crosslinking of the fibrin I or II. Such chelators bind to the calcium, thereby preventing the crosslinking. Any calcium chelator can be utilized. Nonlimiting examples of calcium chelators include citric acid, saccharic acid, ethylenediaminetetraacetic acid (EDTA), nitrilotriacetic acid (NTA), hydroxyethylenediaminetriacetic acid (HEEDTA), ethylenediamindi>o-hydroxyphenylacetic acid! (EDDHA), ethylene-glycolbis (2-aminoethylether) tetraacetic acid (EGTA), diethylenetriaminepentaacetic acid (DTPA), 1,2-diaminocyclohexanetetraacetic acid (DCTA), N,N-bishydroxyethylglycine, 4-(2-hydroxyethyl)-1-piperazineethanesulfonic acid (HEPES) and N-hydroxyethyliminodiacetic acid (HIMDA) and salts thereof, with salts of citric acid being preferred.

Preparation and Concentration of Fibrin Monomer or Non-crosslinked Fibrin from Cell Cultures that Secrete Fibrinogen Any cell culture that can secrete fibrinogen can be utilized in the subject invention. The fibrinogen in the cell culture can be converted to fibrin monomer or noncrosslinked fibrin by the same techniques as those described above with respect to plasma. However, prior to such conversion, it is preferred that the cellular debris be removed.

The process can be carried out as follows: HEPG2 cells are grown and maintained as described by standard texts on mammalian cell culture. The cells are seeded into flasks at a split ratio between 1:4 to 1:8 in Minimal Essential Medium containing 10% calf serum and buffered with 5% CO2.

After 24-36 hours growth at 37 degrees C., the medium is removed and replaced with serum free medium containing a suitable protease inhibitor and 2 1U/ml heparin. Culture is continued for further 24 hour periods with three consecutive changes of serum free media.

The conditioned media is centrifuged at 3,000 grams for 10 minutes to remove any cell debris and the clarified supernatant, which contains fibrinogen, is then gently mixed with a thrombin-like enzyme for 4-5 hours. Preferably, the thrombin-like enzyme is immobilized. A ratio of from about 1.0 ml to about 50 ml., settled volume agarose-thrombin-like enzyme per 500 ml media is suitable. As described above, supports other than agarose can be utilized. The resulting fibrin monomer spontaneously polymerizes and is enmeshed around the immobile support.

The supernatant, which now contains no fibrinogen, is decanted from the support/fibrin gel, which is then washed successfully with four changes of NaCl-0.15 M. at a ratio of from about 10 ml. to about 100 ml. per 1.0 ml original settled volume of support. The washed gel is then semi-dehydrated using a sintered glass funnel under vacuum.

The use of cell cultures that can secrete fibrinogen are preferred when a composition comprising a fibrin monomer is utilized. This is because it is believed that such composition can be utilized to form a fibrin polymer that is useful as a fibrin sealant, regardless of whether the fibrin polymer ultimately crosslinks. Thus, since such cell culture does not contain factor XIII, which is essential for crosslinking, no exogenous factor XIII need be added to make an effective fibrin sealant.
Preparation and Concentration of Fibrin Monomer or Noncrosslinked Fibrin from Recombinant Fibrinogen The noncrosslinked fibrin composition can also be prepared from recombinant fibrinogen. Only recently fibrinogen has been made by recombinant DNA techniques. The resultant fibrinogen composition can then be utilized to produce the composition comprising fibrin monomer or noncrosslinked fibrin by the same techniques as described hereinabove with respect to cell cultures that secrete fibrinogen. However, it is preferred that prior to the formation of the composition comprising fibrin monomer or noncrosslinked fibrin, the cellular debris be removed by the same techniques as described above with respect to cell cultures. The cellular debris can be removed by centrifugation or filtration.

The use of recombinant fibrinogen is preferred when a composition comprising a fibrin monomer is utilized. This is because it is believed that such composition can be utilized to form a fibrin polymer that is useful as a fibrin sealant, regardless of whether the fibrin polymer ultimately crosslinks. Since the recombinant fibrinogen cell culture does not contain factor XIII, which is essential for crosslinking, no exogenous factor XIII need be added to make an effective fibrin sealant.
Solubilization of Noncrosslinked Fibrin The conversion of fibrinogen to noncrosslinked fibrin by, for example, a thrombin-like enzyme, results in the formation of the fibrin in the form of a fibrin hydrogen-bonded polymer. However, as discussed above, it is preferred that the composition comprising noncrosslinked fibrin, and it is essential for the composition comprising fibrin monomer, be in oligomeric or monomeric form. This can be carried out by solubilization of the composition comprising noncrosslinked fibrin.

Solubilization is preferred when the noncrosslinked fibrin is formed by means of a thrombin-like enzyme that is immobilized on a support. This is due to the fact that the use of a thrombin-like enzyme immobilized on a support generally results in the noncrosslinked fibrin hydrogen-bonded polymer being associated with such immobilized enzyme. Thus, since it is preferred that the support not be contained in the resulting composition, solubilization permits one to also remove from the composition comprising noncrosslinked fibrin the support, along with the immobilized enzyme.

Solubilization can be carried out by any technique that is known or to be developed that results in a fibrin monomer. Solubilization can be carried out by contacting the composition comprising noncrosslinked fibrin with a suitable acid buffer solution, preferably an acid buffer having a pH of less than about 5 and preferably from about 1 to about 5. Nonlimiting examples of suitable acid buffer solutions include acetic acid, succinic acid, glucuronic acid, cysteic acid, crotonic acid, itaconic acid, glutamic acid, formic acid, aspartic acid, adipic acid and salts thereof and with succinic acid, aspartic acid, adipic acid and salts of acetic acid being preferred and most preferably sodium acetate. It has been observed that the preferred acid buffers functioned much more efficiently than that of other acid buffers that were tested.

The preferred concentration of the acid buffer is from about 0.02M to about 1M and most preferably from about 0.1M to about 0.3M. Such preferred concentration renders the ionic strength of the composition more biologically compatible.

It is preferred to utilize the least volume of acid buffer possible that still solubilizes the noncrosslinked fibrin to form an aqueous solution comprising fibrin monomer. This results in an aqueous solution comprising fibrin monomer that is highly concentrated in fibrin monomer. Generally, from about 1 ml to about 4 ml of acid buffer per about 1 ml of composition comprising noncrosslinked fibrin is required.

The acid buffer is mixed with the noncrosslinked fibrin and then agitated vigorously for about 1 to 2 minutes to ensure that solubilization is complete.

Solubilization can also be carried out at neutral pH by means of a chaotropic agent. Suitable chaotropic agents include urea, sodium bromide, guanidine hydrochloride, KCNS, potassium iodide and potassium bromide. The preferred concentration of the chaotropic agent is from about 0.2 to about 6.0 molar and most preferably from about 3.5 to about 5.0 molar.

As with the acid buffer, it is preferred to utilize the least amount of chaotropic agent possible that still solubilizes the noncrosslinked fibrin. Generally, from about 1.0 ml to about 1.5 ml of chaotropic agent per about 1 ml of composition comprising noncrosslinked fibrin is required.

The chaotropic agent is mixed with such composition and then agitated vigorously for about 1 to 2 minutes to ensure that solubilization is complete.

Accordingly, solubilization results in a composition comprising a fibrin monomer and, in particular, an aqueous solution comprising fibrin monomer. It is preferred that the fibrin monomer concentration in the aqueous solution be no less than about 10 mg/ml, more preferably from about 20 mg/ml to about 200 mg/ml, even more preferably from about 20 mg/ml to about 100 mg/ml and most preferably from about 25 mg/ml to about 50 mg/ml.

If a thrombin-like enzyme immobilized on a support is utilized that results in such enzyme being present in the composition comprising noncrosslinked fibrin, after solubilization the immobilized enzyme can be removed from the composition comprising the fibrin monomer. This can be carried out by, for example, filtration through any suitable filter that can separate the enzyme. Suitable filters include a sintered polypropylene 20 micron pore size filter from Porex, Inc., a teflon 20-70 micron pore size filter from Fluorotechniques, Inc. or a nylon 66 2246 micron pore size filter from Costar, Inc.

An alternative method for ensuring that no thrombin-like enzyme, e.g., batroxobin, is present in the composition comprising fibrin monomer is to use a soluble thrombin-like enzyme in the system and remove the enzyme following solubilization of the fibrin hydrogen-bonded polymer. The removal of the enzyme can be achieved by use of an affinity matrix, e.g., a ligand bound to an inert support that has a specific affinity for the thrombin-like enzyme or an ion exchange or hydrophobic interaction support or most effectively using the avidin-biotin system.

In this process, biotin is covalently bound to, for example, batroxobin and the biotin-batroxobin conjugate (which is soluble) is directly reacted with plasma, e.g., 10 BU plus 50 ml plasma reacted at 37 degrees C. for 10 minutes. The Fibrin I polymer produced is harvested by centrifugation or filtration and resolubilized in approximately 4 ml 0.2M sodium acetate pH 4.0 containing 30 mM calcium chloride. To the Fibrin I solution is added a molar excess of avidin coupled to an inert support such as agarose. The agarose:avidin:biotin-batroxobin complex is then separated from the Fibrin I by centrifugation or filtration resulting in a composition comprising fibrin monomer that is substantially free of batroxobin, which can be repolymerized as described below to generate a fibrin sealant.

Accordingly, in one embodiment of the present invention, the composition comprising fibrin monomer is substantially free of the thrombin-like enzyme. By substantially free is meant either that all of the thrombin-like enzyme has been removed, or that any thrombin-like enzyme remaining in the composition is at levels insufficient to provide any undesired pharmacological effect. Thus, compositions of this invention desired to be "substantially free" may contain thrombin-like enzyme in an amount between about zero and 10 percent of the original enzyme and preferably between about zero and 2 percent of the thrombin-like enzyme used to prepare the fibrin monomer composition.

Although these embodiments describe compositions wherein the thrombin-like enzyme has been removed following the desired conversion to soluble fibrin, compositions retaining most or all of the thrombin-like enzyme are also believed useful and, as such, are a part of the present invention.

The composition comprising fibrin monomer is now ready for use as a component of the fibrin sealant. It has been observed that when such composition is prepared from whole blood, from about 60% to about 90% of the original fibrinogen is present in the composition, but, of course, in the form of fibrin monomer.

The composition comprising the fibrin monomer can be utilized immediately after it is prepared. In fact, it is particularly preferred to utilize such composition immediately after its preparation when the composition is autologous. If the composition is not utilized immediately after its preparation, the composition can be stored. Storage of the composition requires that the composition be preserved by, for example, freezing or lyophilizing the composition or holding the composition at 4 degrees C. It is believed that the composition in frozen or lyophilized form will be stable for a period of months. When the composition is held at 4 degrees C., it is believed that the composition is stable for at least a period of days.

If the composition is frozen, the composition must be thawed at the time of use. If the composition is lyophilized, at time of use, it is preferred that the composition be reconstituted by the addition of the same acid buffer that was utilized in the solubilization step if that acid was volatile, e.g., acetic acid, or if a choatropic agent was utilized, by the addition of distilled water. As in the solubilization step, in reconstitution the least amount of acid buffer solution or distilled water should be utilized that still results in the fibrin monomer being soluble. In fact, reconstituting a lyophilized composition comprising fibrin monomer can result in an aqueous solution comprising fibrin monomer wherein such monomer concentration is up to 200 mg/ml. Prior to lyophilization, a bulking agent, e.g., mannitol or lactose, can be added to the composition. Alternatively, the lyophilized composition can be utilized in lyophilized form. Such form is particularly preferred when it is desired to add adjuvants, e.g., antibiotics, to the composition.

The composition comprising fibrin monomer can be in virtually any form, for example, a solution, suspension, emulsion or solid, with a solution being preferred. Thus, for example, such composition can be a liquid, gel, paste or salve. Also, of course, the composition can be in the form of a "granule," for example, lyophilized fibrin monomer, that can be, but need not be, treated to form a solution, emulsion or suspension immediately prior to use.

Any suitable solvent can be utilized to form the solution, but, of course, it is preferred that the solvent be nontoxic. Nonlimiting examples of solvents include water, ethyl alcohol, glycerol and propylene glycol, with water being preferred.

An example of a suspension is that the composition comprising fibrin monomer can be mixed with organic solvents, e.g., ethanol, to a final ethanol concentration in excess of 3.0M and shaken. The fibrin monomer will precipitate and can be recovered by centrifugation. The precipitate should be washed with organic phase to remove the aqueous solution used in the solubilization step. An ethanolic suspension of monomeric fibrin can then be applied directly to a bandage or other carrier or even applied directly to a wound site. The organic phase is allowed to evaporate. In the case of a bandage or other carrier the suspension can be rehydrated by contacting with the site of application or some other means, and the fibrin allowed to polymerize.

Alternatively, an organic suspension of fibrin monomer prepared in a highly volatile phase, e.g., diethyl ether, might be atomized and delivered as a spray suspension to the desired site. It is preferable that the volatile phase is non-flammable. It is possible that an organic suspension of fibrin monomer could be delivered to the ear, nose, throat, or lungs by spray or breathing or delivered to a bleeding oesophageal or gastric lesion by injestion.

The Uses of the Fibrin Sealant of the Subject Invention

The fibrin sealant of the subject invention is utilized by contacting the desired site with the composition comprising fibrin monomer or noncrosslinked fibrin and converting the fibrin monomer to fibrin polymer or noncrosslinked fibrin to crosslinked fibrin concurrently with said contacting step, thereby forming the fibrin clot. The supplement can be added to the portion containing the fibrin monomer or noncrosslinked fibrin, can be independently administered to the desired site so as to intimately mix with the fibrin polymer or noncrosslinked fibrin so that the supplement becomes suspended within the fibrin clot, or can be added to the composition that causes the fibrin monomer or noncrosslinked fibrin to form the fibrin clot. The supplement is held within the fibrin clot such that the supplement is slowly released over time due to leaching and/or breakdown of the fibrin clot, as a result of the normal healing process that follows. The amount of supplement may vary depending on the type of supplement or combination of supplements employed, the size of the fibrin clot, location within the body and type of tissue being treated, and so forth.

For the purpose of the subject invention "desired site" is that location where one desires to form the fibrin clot. What or where the desired site is depends on the use of the fibrin sealant of the subject invention. Also, it should be noted that it is believed that the fibrin sealant can be utilized not only in humans but also in other mammals. Also, if the source of the fibrin sealant is blood, then it is preferred, but not essential, that the blood be derived from the same species that the fibrin sealant will be utilized.

The fibrin sealant of the subject invention can be utilized for any use that is known or to be developed for a fibrin sealant. The methods, kits or fibrin sealant of the subject invention can be used for connecting tissues or organs, stopping bleeding, healing wounds, sealing a surgical wound, use in vascular surgery include providing hemostasis for stitch hole bleeding of distal coronary artery anastomoses; left ventricular suture lines; aortotomy and cannulation sites; diffuse epimyocardial bleeding seen in reoperations; and oozing from venous bleeding sites, e.g. at atrial, caval, or right ventricular levels. The subject invention is also useful for sealing of dacron artery grafts prior to grafting, sealing tissues outside the body, producing fibrin rafts for cell growth, stopping bleeding from damaged spleens (thereby saving the organ), livers, and other parenchymatous organs; sealing tracheal and bronchial anastomoses and air leaks or lacerations of the lung, sealing bronchial stumps, bronchial fistulas and esophageal fistulas; for sutureless seamless healing ("Zipper" technique), and embolization in vascular radiology of intracerebral AVM's, liver AVM's, angiodysplasia of colon, esophageal varices, "pumping" GI bleeders secondary to peptic ulcers, etc. The subject invention is further useful for providing hemostasis in corneal transplants, nosebleeds, post tonsillectomies, teeth extractions and other applications. Also, the fibrin sealant of the subject invention is especially suited for individuals with coagulation defects. Likewise, the fibrin sealant can be administered by spinal injections to treat low back pain brought about by the condition known as "leaky disc syndrome". See in this regard U.S. Pat. No. 6,468,527, incorporated herein by reference. Thus when a corticosteroid is used as the supplement, the fibrin sealant is delivered to a desired target in the body such as a target that is inflamed. The fibrin sealant serves to hold the supplement in place, providing a prolonged, time-released administration of corticosteroid (or any other supplement). The corticosteroid may be, for example, triamicinalone or methylprednisolone. The fibrin sealant infused with corticosteroid may be delivered by, for example, fluoroscopic transforaminal lumber epidural or intra-discal injection, such as described in U.S. Pat. No. 6,468,527.

The dosage of the composition comprising fibrin monomer and supplement or composition comprising noncrosslinked fibrin and supplement depends on the particular use of the fibrin sealant, but the dosage should be an effective amount for the composition to perform its intended use. Generally, for a composition comprising fibrin monomer that is an aqueous solution, it is believed that from about 3 ml to about 5 ml of such composition is sufficient to be an effective fibrin sealant. However, depending on the use of the composition, the dosage can range from about 0.05 ml to about 40 ml Also, if a composition comprising noncrosslinked fibrin in polymer form is utilized or the composition is in solid form, then the composition should contain that amount of fibrin that is in such aqueous solution.

The Administration of the Fibrin Sealant of the Subject Invention

As used herein, a "contacting step" includes contact by means of dripping, spraying, injecting, or mixing.

For the purpose of the subject invention the conversion of the fibrin monomer to fibrin polymer or noncrosslinked fibrin to crosslinked fibrin "concurrently" with said contacting step means that such conversion step and such contacting step occur within a time period of each step so as to form the fibrin clot at the desired site. Thus, concurrently can mean that after the contacting step, the fibrin monomer is converted to fibrin polymer or the noncrosslinked fibrin is converted to crosslinked fibrin. This is carried out by contacting the composition comprising fibrin monomer or noncrosslinked fibrin, after such composition has been applied to the desired site, with a composition that can convert the fibrin monomer to fibrin polymer or the noncrosslinked fibrin to crosslinked fibrin. The conversion step should generally occur within about 0.5-1.5 minutes after the contacting step. This is particularly the case within an enclosed cavity such as a joint capsule or spinal disc, in the absence of major disruptions or tears in the capsule or disc. Otherwise, the composition comprising the fibrin monomer or noncrosslinked fibrin, especially if the noncrosslinked fibrin is a fibrin monomer, may flow away from the desired site.

Concurrently can also mean that the contacting step and converting step take place simultaneously. This is carried out by contacting the desired site with the composition comprising the fibrin monomer or noncrosslinked fibrin at the same time that such composition is contacted with a composition that can convert the fibrin monomer to fibrin polymer or the noncrosslinked fibrin to crosslinked fibrin.

Finally, and preferably, concurrently can also mean that the conversion step can commence prior to the contacting step, albeit not so far prior to the contacting step that all of the fibrin monomer has been converted to fibrin polymer or all of the noncrosslinked fibrin has been converted to crosslinked fibrin. Otherwise, all of the fibrin monomer will be converted to fibrin polymer or all of the noncrosslinked fibrin will be converted to crosslinked fibrin, prior to the contacting step, which results in a very poor fibrin sealant. This embodiment is carried out by mixing the composition comprising the fibrin monomer or noncrosslinked fibrin with a composition that can convert the fibrin monomer to fibrin polymer or the noncrosslinked fibrin to crosslinked fibrin, prior to the contacting step. Since it takes about 30 seconds for the conversion step to be complete, the conversion step should not begin more than about 30 seconds and preferably not more than about 3 seconds prior to the contacting step. This embodiment is preferred because it ensures that the maximum amount of the composition comprising the fibrin monomer or noncrosslinked fibrin will remain at the desired site and yet also forms an excellent fibrin clot.

Conversion of the Composition Comprising Fibrin Monomer to Fibrin Polymer or Noncrosslinked Fibrin to Crosslinked Fibrin The conversion of the fibrin monomer to fibrin polymer or the noncrosslinked fibrin to crosslinked fibrin can be carried out by any technique that is known or to be developed. However, how the conversion step is carried out depends on the source of the composition comprising fibrin monomer or noncrosslinked fibrin e.g., whole blood or recombinant fibrinogen, the form of the fibrin monomer or noncrosslinked fibrin, e.g., fibrin I or des BB fibrin, and, to a lesser extent, whether the desired site will contain the patients blood or other body fluids at the time of use of the fibrin sealant.

Also, if a separate composition, such as an alkaline buffer, is utilized (discussed below) for the conversion step, then the method of the subject invention can be carried out with, for example, a multi-barreled syringe. The multi-barreled syringe can be tipped with a Y-shaped, or cone-shaped end chamber, thereby permitting the mixing of the composition comprising fibrin monomer or noncrosslinked fibrin and the composition to be utilized in the conversion step to mix immediately prior to the contacting step. Also, rather than a Y-shaped multi-barreled syringe, or mixing chamber-tipped barrel syringe, a multi-barreled syringe with multiple openings can be utilized. This permits the simultaneous contacting of the desired site and conversion to fibrin polymer or crosslinked fibrin to take place. Also, the compositions of the multi-barreled syringe or mixing chamber-tipped barrel syringe can be sprayed onto the desired site.

Blood as the Source of the Composition Comprising Fibrin Monomer or Noncrosslinked Fibrin If the source of the composition comprising fibrin monomer or noncrosslinked fibrin is blood, then as discussed above, it is believed that the composition will retain enough prothrombin, factor XIII and other necessary substances to convert such fibrin monomer or noncrosslinked fibrin to crosslinked fibrin, e.g., activators of prothrombin. If the noncrosslinked fibrin is a fibrin polymer, i.e., the noncrosslinked fibrin has not been solubilized, the noncrosslinked fibrin can be converted to crosslinked fibrin by the activation of prothrombin and factor XIII of such composition to form crosslinked fibrin. Such activation can be carried out by contacting the composition with a source of calcium ions. Nonlimiting sources of calcium ions include calcium chloride, preferably at a concentration of 30 mM. Alternatively, and less preferred, the calcium ions can be supplied by the blood at the desired site. Calcium ions may also be supplied by the addition of the patients own blood to the mixture, which is supplied in the form of an injected "blood patch". The use of autologous blood or blood plasma as a blood patch has been described in literature. Spine specialists have been known to inject blood into a patients spinal disc in an attempt to seal a ruptured or leaking disc by utilizing the natural clotting properties of the patients own blood. Results from this technique were limited and have not been shown to have adequate effect to justify incorporation into normal practice. There are also published articles describing the use of epidural blood patching in both the prevention and the treatment of post-dural puncture headache. Dural puncture is a common procedure, but leakage of CSF from the resulting dural defect may cause postural headache after the procedure, and this can be disabling. Injecting an epidural blood patch around the site of the defect may stop this leakage, and so may have a role in preventing or treating post dural puncture headache. Hence, it is believed that calcium ions may be supplied in adequate quantity from a blood in a blood patch to facilitate activation.

If the noncrosslinked fibrin has been solubilized, i.e., is a fibrin monomer, how the fibrin monomer is converted to crosslinked fibrin depends on how the solubilization was carried out. If the noncrosslinked fibrin was solubilized by an acid buffer, the crosslinked fibrin can be formed by raising the pH of the composition comprising fibrin monomer such that the fibrin monomer can polymerize. This can be carried out by contacting such composition with any suitable alkaline buffer. Nonlimiting examples of suitable alkaline buffers include HEPES, sodium hydroxide, potassium hydroxide, calcium hydroxide, bicarbonate buffers such as sodium bicarbonate and potassium bicarbonate, tri-metal salts of citric acid, salts of acetic acid and salts of sulfuric acid. Preferred alkaline buffers include: 0.5-0.75M Sodium carbonate/bicarbonate pH 10-10.5, 0.5-0.75M Sodium bicarbonate/NaOH pH 10.0, 1.5M Glycine/NaOH pH 10.0, 0.5-1.0M Bis hydroxeythylaminoethane sulphonic acid (BES) pH 7.5, 1M Hydroxyethylpiperazine propane sulphonic acid (EPPS) pH 8.5, 0.5M Tricine pH 8.5, 1M Morpholino propane sulphonic acid (MOPS) pH 8.0, 1M Trishydroxymethyl aminoethane sulphonic acid (TES) pH 8.0 and 0.5M Cyclohexylaminoethane sulphonic acid (CHES) pH 10.0; with 0.5-0.75M Sodium carbonate/bicarbonate pH 10-10.5, 0.5-1.0M Bis hydroxeythylaminoethane sulphonic acid (BES) pH 7.5, 1M Hydroxyethylpiperazine propane sulphonic acid (EPPS) pH 8.5 and 1M Trishydroxymethyl aminoethane sulphonic acid (TES) pH 8.0 being most preferred.

The amount of alkaline buffer that is utilized should be enough to polymerize the noncrosslinked fibrin. It is preferred that about 10 parts to about one part of composition comprising fibrin monomer be mixed with about 1 part alkaline buffer. It is even more preferred that such ratio be about 9:1. It should be noted that the preferred ratio depends on the choice of buffer and the desired "strength" of the fibrin polymer. Of course, the desired strength of the fibrin polymer depends on the end-use of the fibrin sealant.

If the solubilization was carried out with a chaotropic agent, then the fibrin monomer can be converted to crosslinked fibrin by diluting the composition comprising fibrin monomer with, for example, distilled water. The dilution should be carried out such that the minimal amount of diluent is utilized. Generally; the resulting concentration of the chaotropic agent after dilution should be from about 0.5 to about 0.1 molar.

In addition to raising the pH or diluting the chaotropic agent of the composition comprising fibrin monomer, it is preferred that the prothrombin and factor XIII of such composition be activated to form the crosslinked fibrin. Such activation can be carried out by the contacting the composition with a source of calcium ions. The source of the calcium ions can be part of the alkaline buffer or part of the acid buffer that is utilized in the solubilization step. Nonlimiting sources of calcium ions include calcium chloride, preferably at a concentration of 30 mM. Alternatively, and less preferred, the source of calcium ions can be supplied by the blood at the desired site.

It should be noted that if the alkaline buffer is a carbonate/bicarbonate buffer, then the source of calcium ions must be added to the acid buffer during the solubilization step. This is due to the fact that the calcium chloride is not soluble in the carbonate/bicarbonate buffer. It is preferred that the concentration of calcium ions in the acid buffer solution be from about 5 millimolar to about 150 millimolar and more preferably from about 5 mM to about 50 mM.

It is believed that the resulting fibrin clot will be crosslinked fibrin II, regardless of which form of noncrosslinked fibrin, i.e., fibrin monomer or fibrin polymer, is present. However, if the form of noncrosslinked fibrin is des BB fibrin, then it is believed that in addition a source of additional thrombin or thrombin-like enzyme may be required to convert des BB fibrin to crosslinked fibrin. Such a source of thrombin can be, for example, plasma from the patient wherein such plasma is added to the composition comprising noncrosslinked fibrin.

If the desired site contains blood and a composition comprising a fibrin monomer is utilized, i.e., the noncrosslinked fibrin has been solubilized, then this blood can be utilized as a diluent of the chaotropic agent or to raise the pH of the composition comprising fibrin monomer. Thus, no diluent or alkaline buffer need be utilized. In this embodiment, it is preferred that the source of calcium ions be contained in the acid buffer or chaotropic agent utilized in the solubilization step. Also, in this embodiment the composition comprising fibrin monomer can be placed on a solid support, e.g., bandage, suture, prosthesis, or dressing, that will be in contact with the desired site. Such support is then placed in contact with the desired site until, for example, the fibrin clot forms.

However, it should be noted, that if the composition comprising fibrin monomer does not retain enough prothrombin and factor XIII so as to form crosslinked fibrin, such composition is still useful as a fibrin sealant because the polymerization of fibrin monomer per se is useful to form a fibrin clot. Also, such composition can still be utilized to form crosslinked fibrin by the addition of a source of calcium ions and activated factor XIII (or precursors to activated factor XIII) and, optionally, thrombin. Such source of calcium ions, activated factor XIII and thrombin can be added to the compositions comprising fibrin monomer. The activated factor XIII can be added to the composition comprising fibrin monomer at a final concentration of from about 1.0 to about 20 units factor XIII per ml of composition comprising noncrosslinked fibrin. Alternatively, the factor XIII can be supplied by the blood or body fluids at the desired site or by the addition of autologous plasma to the composition comprising fibrin monomer. Nonlimiting sources of calcium ions include calcium chloride, preferably at a concentration of 30 mM. Alternatively, and less preferred, calcium ions can be supplied by the blood or body fluids at the desired site. From about 4 units to about 500 units of thrombin per ml. of composition comprising fibrin monomer can be added or the thrombin can be provided by the desired site.

Cell Cultures that Secrete Fibrinogen or Recombinant Fibrinogen as the Source of the Composition Comprising Fibrin Monomer or Noncrosslinked Fibrin If the source of the composition comprising noncrosslinked fibrin are cell cultures that secrete fibrinogen or recombinant fibrinogen, and the noncrosslinked fibrin is a fibrin polymer, i.e., the noncrosslinked fibrin has not been solubilized, then a source of calcium ions and activated factor XIII (or precursors to activated factor XIII) must be utilized to form crosslinked fibrin. Factor XIII must be utilized because these sources of noncrosslinked fibrin do not contain any factor XIII. The activated factor XIII can be added to the composition comprising noncrosslinked fibrin at a final concentration of from about 1.0 to about 20 units factor XIII per ml of composition comprising noncrosslinked fibrin. Alternatively, the factor XIII can be supplied by the blood or body fluids at the desired site or by the addition of autologous plasma to the composition comprising noncrosslinked fibrin. Nonlimiting sources of calcium ions include calcium chloride, preferably at a concentration of 30 mM. Alternatively, calcium ions can be supplied by the blood or body fluids at the desired site. Also, as an option, thrombin or thrombin-like enzyme can be added to such composition in order to ensure that crosslinked fibrin II is formed. From about 4 units to about 500 units of thrombin per ml of composition comprising noncrosslinked fibrin can be added or the thrombin can be provided by the desired site.

If the noncrosslinked fibrin has been solubilized, i.e., is a fibrin monomer, how the fibrin monomer is converted to fibrin polymer depends on how the solubilization was carried out, e.g., acid buffer or chaotropic agent. The formation of fibrin polymer can be carried out by the same methods as described above. This fibrin polymer, if desired, can then be converted to crosslinked fibrin by the addition of a source of calcium ions and activated factor XIII (or precursors to activated factor XIII) and, optionally, thrombin to the composition comprising fibrin monomer, as described above. The activated factor XIII can be added to the composition comprising noncrosslinked fibrin at a final concentration of from about 1.0 to about 20 units factor XIII per ml of composition comprising noncrosslinked fibrin. Alternatively, the factor XIII can be supplied by the blood or body fluids at the desired site or by the addition of autologous plasma to the composition comprising noncrosslinked fibrin. Nonlimiting sources of calcium ions include calcium chloride, preferably at a concentration of 30 mM. Alternatively, and less preferred, calcium ions can be supplied by the blood or body fluids at the desired site. From about 4 units to about 500 units of thrombin per ml. of composition comprising fibrin monomer can be added or the thrombin can be provided by the desired site.

Fibrin Sealant Adjuvants

The fibrin sealant of the subject invention can also contain adjuvants, for example, antibiotics, e.g., gentamycin, cefotaxim, nebacetin and sisomicin, histaminine $H_2$-antagonists, e.g., ranitidine, and anticancer drugs, e.g., OK-432. This can be carried out by adding the desired antibiotic to the composition comprising fibrin monomer or noncrosslinked fibrin. Other adjuvants can also be added, for example, fibronectin, fibrinolytic inhibitors such as aprotinin, alpha-2 antiplasmin, PAI-1, PAI-2, 6-aminohexanoic acid, 4-aminomethyl cyclohexanoic acid, collagen or keratinocytes. It is believed that the dosage of such adjuvant is the same as that utilized in conventional fibrin sealants.

Fibrin Sealant Kits

The subject invention also provides fibrin sealant kits. The kit can contain as a first component a composition comprising fibrin monomer and a second component an alkaline buffer that is capable of polymerizing the fibrin monomer or distilled water, depending on how the solubilization step was performed. The second component can optionally contain a source of calcium ions. Alternatively, the first component can be a composition comprising noncrosslinked fibrin and the second component can be a source of calcium ions. If the source of fibrinogen utilized to prepare a composition comprising noncrosslinked fibrin is from cell cultures that secrete fibrinogen or recombinant fibrinogen, the first component can be a composition comprising noncrosslinked fibrin, the second component can be a source of calcium ions and a third component is activated factor XIII.

Additionally, the kit may have a "trigger-activated" delivery mechanism such as pistol-shaped delivery gun, which includes a multi-port cartridge holder mounted thereon. The cartridge holder would allow for the independent mounting of multiple components to the proprietary mixture to be delivered to the application site. These components may include, but are not limited to the components of the fibrin sealant, contrast medium, therapeutic additives, such as drugs and blood or plasma utilized as a blood patch, (described previously). These cartridges may be individually or multiplely activated to deliver varying amounts of material in measured doses with each pull of the trigger.

It should be emphasized that although the method of the present invention was described with a-specific number and sequence of steps, these steps can be altered or omitted while other steps may be added without departing from the scope of the invention. As such, the specific steps discussed in the preferred embodiment of the present invention illustrate just one example of how to utilize the novel method and steps of the present invention.

What is claimed is:

1. A method of treating tissue of a patient wherein the tissue is a disc that has at least one defect, comprising: inserting a needle through skin and into the disc, injecting a composition through the needle into the disc using a trigger-activated delivery gun to deliver a measured dose of the composition with each pull of the trigger, wherein the gun has the needle affixed thereto, wherein the gun includes a tip such that mixing of the composition occurs prior to the composition contacting the disc, wherein the composition comprises at least one supplement, a contrast medium, autologous fibrinogen and a snake venom effective to convert the autologous fibrinogen to fibrin, and wherein the composition forms fibrin.

2. The method of claim 1, wherein the at least one supplement is selected from the group consisting of analgesics, anesthetics, antimicrobial compounds, antibiotics, antifibrinolytic agents, anti-inflammatory compounds, antibodies, anticoagulants, antifungal compounds, antiangiogenins, antiseptics, cardiovascular drugs, cytokines, cytotoxins or cell proliferation inhibiting compounds, chemotherapeutic drugs, interferons, growth factors, hormones, lipids or liposomes, oligonucleotides or polynucleotides, osteoinducers, cartilage-inducing compounds, polymers, polysaccharides, proteoglycans, polypeptides, protease inhibitors, steroids, vasoconstrictors, vasodilators, vitamins, nutritional supplements, minerals, stabilizers and combinations thereof.

3. The method of claim 1, wherein the at least one supplement is an anesthetic.

4. The method of claim 1, wherein the at least one supplement is growth hormone.

5. The method of claim 1, wherein the disc has at least one defect in the annulus fibrosus.

\* \* \* \* \*